United States Patent [19]

Neufeld

[11] 4,327,909

[45] May 4, 1982

[54] RESILIENT SLING

[76] Inventor: Alonzo J. Neufeld, 1650 N. Parway Dr., Glendale, Calif. 91206

[21] Appl. No.: 200,445

[22] Filed: Oct. 24, 1980

[51] Int. Cl.³ .............................................. A63B 21/02
[52] U.S. Cl. ...................................... 272/137; 128/94
[58] Field of Search ................. 128/94, 77; 273/29 A; 272/142, 135, 137

[56] References Cited

U.S. PATENT DOCUMENTS

| | | | |
|---|---|---|---|
| 3,529,820 | 9/1970 | Templeton | 272/137 |
| 3,554,194 | 1/1971 | Johnson | 128/94 |
| 4,214,579 | 7/1980 | Ford | 128/94 |

*Primary Examiner*—Richard C. Pinkham
*Assistant Examiner*—William R. Browne
*Attorney, Agent, or Firm*—Harlan P. Huebner

[57] ABSTRACT

A resilient sling for use with and to support a fractured arm of a wearer whereby a low energy exercise of the muscles and joints of the arm is possible utilizing the sling. When the arm is moved downward within the sling both will flex and stretch downward and offer slight resistance to the movement of the arm and upon controlled release of the arm the sling will return to an upper at rest position moving the arm upward therewith. Such exercising will promote healing of the fracture and prevent joint and muscle stiffness.

2 Claims, 3 Drawing Figures

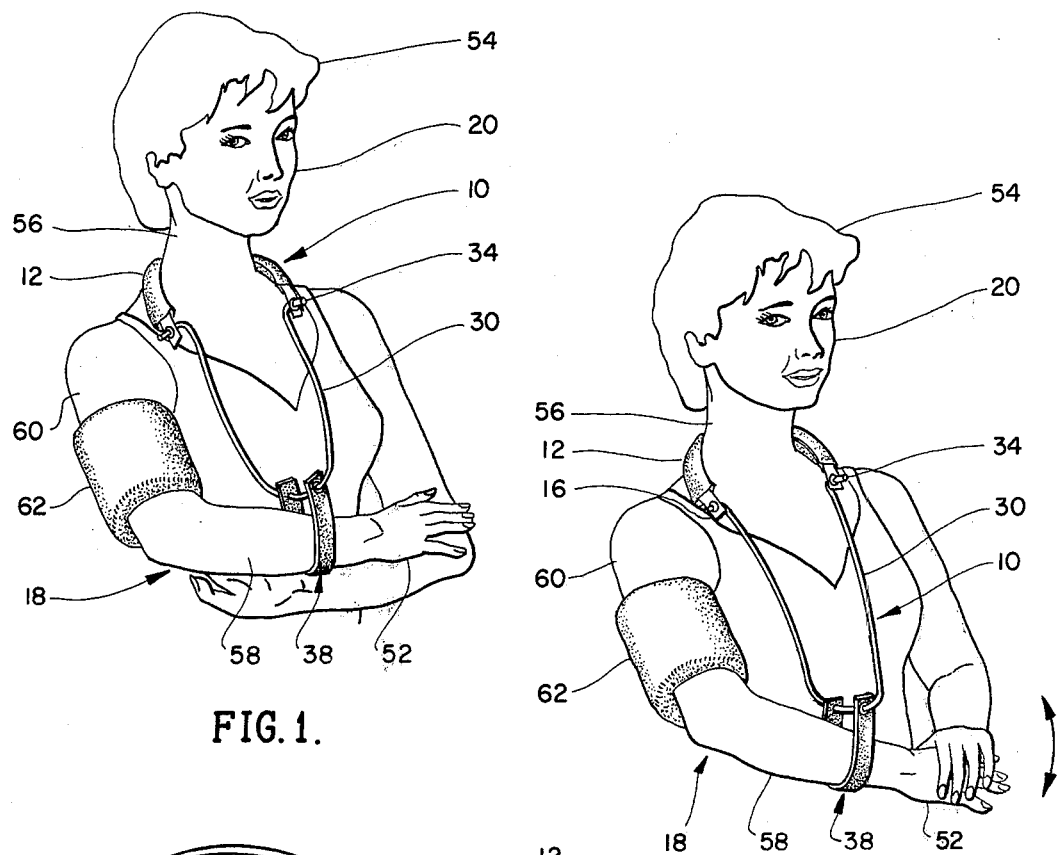
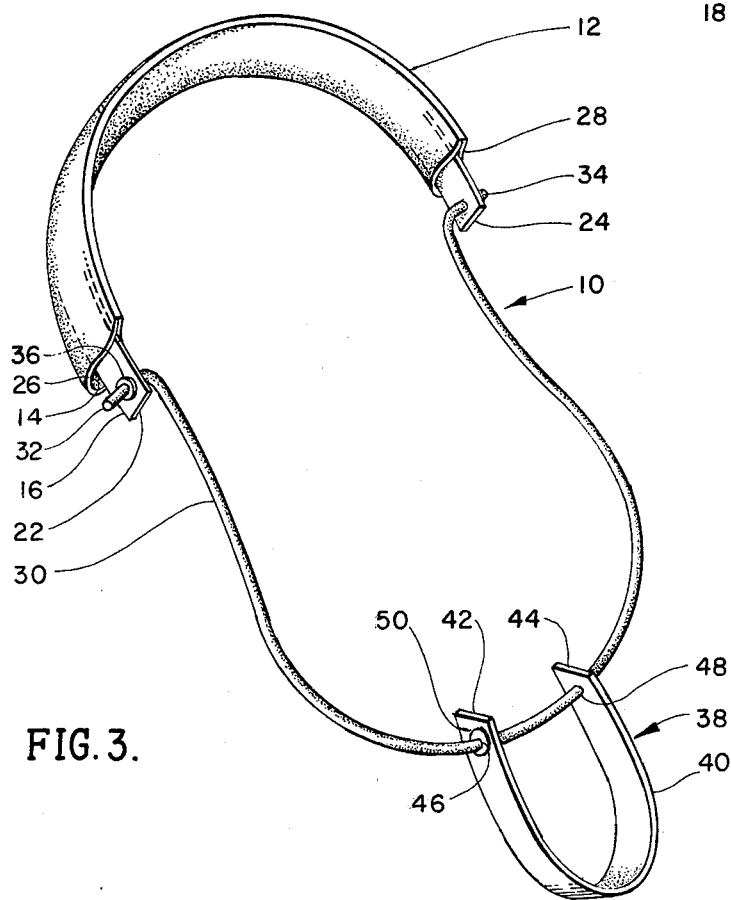
FIG. 1.
FIG. 2.
FIG. 3.

RESILIENT SLING

BACKGROUND OF THE INVENTION

Heretofore, it has been the consensus of the medical profession and orthopedic specialists that a fracture of bones in the upper limbs and shoulders of humans required complete immobility of the limb during the healing process.

To that end elaborate slings have been used to rigidly maintain the arm or limb in a fixed position and preferably snug to the body.

While healing of the fractures have resulted by this immobility, the after effects to muscles and joint functions due to atrophy have caused stiffness. In some cases loss of properly functioning joints have rendered the limb almost useless.

With the advent of new medical techniques the medical profession has found that the majority of upper limb and shoulder fractures heal more rapidly with limited exercising of the limb. This exercising permits muscle and joint functioning and prevents stiffness of the joint, muscle and limb.

SUMMARY OF THE INVENTION

It is therefore, an object of this invention to provide a resilient sling for an arm which is capable of stretching movement and return to its normal at rest position.

Another object of the invention is to provide a resilient sling of simple construction and light-weight.

A further object of the invention is to provide a resilient sling wherein slight downward pressure can be exerted by the forearm and the sling be stretched moving with the arm. Upon release of the forearm the sling being of a resilient nature will move upwardly carrying the forearm either unrestricted or controlled.

Another object of the invention is to provide a resilient sling including an expandable arm retainer adapted to fit over an unusually large hand or a bandage.

Another object of the invention is to provide a resilient sling including a pading element around the neck to prevent soreness and cutting into the neck of the sling when it is being used.

These and other objects and advantages will become apparent from the following part of the specification wherein details have been described for the competence of disclosure, without intending to limit the scope of the invention which is set forth in the appended claims.

BRIEF DESCRIPTION OF THE DRAWINGS

These advantages may be more clearly understood from the following detailed description and by reference to the drawings in which:

FIG. 1 is an environmental view of the resilient sling in an at rest position on a wearer;

FIG. 2 is a view similar to FIG. 1 wherein the wearer has moved the forearm downward and stretched the sling; and FIG. 3 is a perspective view of the resilient sling.

DETAILED DESCRIPTION OF THE PREFERRED EMBODIMENT

Now referring specifically to FIG. 3 which is a detailed structural drawing of a form of the invention, there is illustrated an elastic sling generally designated 10.

The sling 10 includes a neck portion, pad or band 12 which in the preferred embodiment is an elongated tubular piece of material. The band 12 includes a passage 14 through which a strap 16 may extend. Preferably the pad or band 12 is made from a soft thick material to absorb the pressure of an arm 18 or a wearer 20. As for the strap 16 it can be formed of canvas belting or any other material with strength to support the weight of the arm.

As can be seen in the drawings the strap 16 is of a sufficient length to have ends 22 and 24 project beyond the ends 26 and 28 of the pad or band 12.

By having the pad or band 12 tubular the strap 16 may be shifted therein to achieve a balancing and comfortable position for the wearer 20 when the sling 10 is in place encompassing the forearm 58.

An an alternative without departing from the spirit of the invention neck portion 12 and the strap 16 could be made from a single piece of material.

The sling 12 has attached to the ends 22 and 24 of strap 16 an elastic band 30 with ends 32 and 34. The elastic band 30 is preferably secured to the strap 16 by passing from the inside through the strap 16 to the outside where conventional grommets 36 secure the band 30 near its respective ends 32 and 34 to the strap 16.

Secured on the elastic band 30 at the bottom of the curve is a forearm retainer or holder means 38. The holder 38 includes a flat strap 40 with ends 42 and 44. The strap 40 includes openings 46 and 48 punched or otherwise formed therethrough adjacent ends 42 and 44. The inventor preferably secures grommets 50 to the strap 40 so that the ends 42 and 44 may be moved apart or together dependent upon circumstances such as the size of the wearer's 20 hand 52.

The elastic band 30 is made of natural rubber, synthetic rubber or other elastomers to accomplish the intended purpose. Depending upon the modulus of elasticity desired, bands 30 of different density of rubber may be provided. Also the band 30 can be tubular, tubular and hollow or a flat band without departing from the spirit of the invention.

In operation the wearer 20 places the elastic sling 10 over his or her head 54 with the neck-pad 12 in place around the neck 56 allowing the elastic band 30 to hang down in front of the wearer 20. This is illustrated in FIGS. 1 and 2 of the drawing.

Next, dependent upon the arm 18 which has the fracture, the hand 52 is passed through the forearm holder or retainer 38 so it will engage the forearm 58. With the expandable contraction feature of the holder 38, it being spreadable to widen the opening, it will accommodate being passed around a large hand 52 or portion of the forearm 58 or hand 52 which may be bandaged. Additionally, with the adjustability of the forearm retainer 38 once it is in place around the forearm 58 the ends 42 may be moved toward each other and clamp or lock the sling 10 in place. The grommets 46 will prevent the holder 38 from becoming disengaged unless moved by the other hand of the wearer 20 or other person assisting the wearer.

In the case of the illustration in FIGS. 1 and 2, the wearer 20 has a fracture of the upper arm 60, and the fracture is surrounded by an appropriate bandage, cast or splint arrangement 62.

With the sling 10 in place there is an at rest or first position, seen in FIG. 1, wherein the forearm 58 is generally horizontal. This position is the usual position to carry the arm 18 to achieve the usual immobility. Depending upon the modulus of elasticity of the band 30 the arm 18 may or may not be left unsupported other than by the sling 10. If however, modulus of elasticity is relatively weak the other hand may be needed to assist in supporting the forearm 58.

In order to commence exercising of the limb with the fracture, the low energy exercise may be started. With the left hand, in the case of the illustrations, the right hand 52 pushes the forearm 58 downward, as seen in FIG. 2, from the horizontal. This stretching to a second position causes stimulation and movement of joints and muscles in the forearm 58 and upper arm 60.

Because of the resiliency of the band 30 it will then endeavor to return to its original at rest position. If the forearm 58 were left unassisted then the reflex unrestricted return might cause more injury to the joint. Therefore, it is preferred during the initial exercise stages to prevent the unrestricted return by applying compensating opposite pressure on hand 52 by the other hand as seen in FIG. 2.

As the arm 18 heals and the joints and muscles loose their stiffness, then the forearm 58 may be moved up and down in sling 10 under its own control. Also, by increasing the range of movement or the rate of up and down motion within the painless range healing is promoted, also stiffness of joints is relieved. It has been found that the healing is promoted by the movement of muscles in the upper arm 60 over the fracture area.

It should also be appreciated that the modulus of elasticity of the band 30 may be varied depending on the weight and size of the wearer and also on the state of recovery.

The invention and its attendent advantages will be understood from the foregoing description and it will be apparent that various changes may be made in the form and method of making, construction and arrangements of the parts without departing from the spirit and scope thereof or sacrificing its material advantages, the arrangements herein before described being merely by way of example. I do not wish to be restricted to the specific forms shown, method, or uses mentioned, except as defined in the accompanying claims, wherein various portions have been separated for clarity of reading and not for emphasis.

I claim:

1. A resilient sling for use with the arm of a wearer whereby a low energy exercise of the arm is possible within the sling wherein the sling includes:
   a neck portion adapted to encircle the back of the neck of said wearer and having two ends projecting downwardly in front of said wearer;
   a resilient band portion forming a continuation of said neck portion between said ends of said neck piece creating an endless loop;
   a forearm strap holder means separate from said endless loop and of a width greater than said resilient band portion having two ends and said forearm strap holder means adapted to receive and maintain the forearm of said wearer in a generally single area of said forearm and said two ends of said forearm strap holder means slidably mounted on said resilient band portion;
   and resilient band capable of being stretched from an at rest position generally horizontal position through a low energy exercise of said forearm downwardly limited only by anatomic limitations by downward pressure of said forearm against said resilient band, and said resilient band of such a modulus of elasticity as to return to its normal at rest position upon the appropriate release of downward pressure of said forearm; and
   said neck portion comprising a tubular member and a strap portion of a length greater than said tubular member being shiftable therethrough and with ends of said strap member projecting beyond the ends of said tubular member.

2. A resilient sling as defined in claim 1 wherein:
   said neck portion is a hollow padded tubular member;
   a strap portion of a length greater than said neck portion passes through said hollow member with end projecting beyond the ends of said neck portion;
   said resilient band is secured to the ends of said strap; and
   said ends of said forearm strap holder capable of moving toward and away from each other to enlarge or contract the area of said forearm contact.

* * * * *